US009670164B2

(12) United States Patent
Yang et al.

(10) Patent No.: US 9,670,164 B2
(45) Date of Patent: Jun. 6, 2017

(54) PROCESSES FOR THE PREPARATION OF PESTICIDAL COMPOUNDS

(71) Applicant: Dow AgroSciences LLC, Indianapolis, IN (US)

(72) Inventors: Qiang Yang, Zionsville, IN (US); Beth Lorsbach, Indianapolis, IN (US); Greg Whiteker, Carmel, IN (US); Carl DeAmicis, Indianapolis, IN (US); Kaitlyn Gray, Freeland, MI (US); Yu Zhang, Carmel, IN (US); Joseck M. Muhuhi, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/243,352

(22) Filed: Aug. 22, 2016

(65) Prior Publication Data
US 2016/0368880 A1    Dec. 22, 2016

Related U.S. Application Data

(62) Division of application No. 14/989,269, filed on Jan. 6, 2016, now Pat. No. 9,447,048, which is a division of application No. 14/718,621, filed on May 21, 2015, now Pat. No. 9,260,396, which is a division of application No. 14/517,595, filed on Oct. 17, 2014, now Pat. No. 9,085,564.

(60) Provisional application No. 62/034,456, filed on Aug. 7, 2014, provisional application No. 62/001,925, filed on May 22, 2014, provisional application No. 61/892,124, filed on Oct. 17, 2013.

(51) Int. Cl.
*C07D 231/40* (2006.01)
*C07D 401/14* (2006.01)
*A01N 43/56* (2006.01)
*C07D 401/04* (2006.01)
*C07D 231/38* (2006.01)

(52) U.S. Cl.
CPC .......... *C07D 231/40* (2013.01); *A01N 43/56* (2013.01); *C07D 231/38* (2013.01); *C07D 401/04* (2013.01); *C07D 401/14* (2013.01)

(58) Field of Classification Search
CPC .................................................. C07D 231/40
USPC ...................................................... 548/372.5
See application file for complete search history.

(56) References Cited

U.S. PATENT DOCUMENTS

| | | |
|---|---|---|
| 3,597,341 A | 9/1968 | Alexis |
| 4,080,457 A | 3/1978 | Harrison et al. |
| 4,260,765 A | 4/1981 | Harrison et al. |
| 4,407,803 A | 10/1983 | Haviv et al. |
| 4,536,506 A | 8/1985 | Marcoux et al. |
| 4,556,671 A | 12/1985 | Copp et al. |
| 4,810,719 A | 3/1989 | Appleton et al. |
| 4,824,953 A | 4/1989 | Bronn |
| 5,220,028 A | 6/1993 | Iwasawa et al. |
| 5,625,074 A | 4/1997 | Daum et al. |
| 5,631,380 A | 5/1997 | Haas et al. |
| 5,652,372 A | 7/1997 | Muller et al. |
| 5,693,657 A | 12/1997 | Lee et al. |
| 5,750,718 A | 5/1998 | Muller et al. |
| 5,817,677 A | 10/1998 | Linz et al. |
| 5,854,264 A | 12/1998 | Anthony et al. |
| 5,854,265 A | 12/1998 | Anthony et al. |
| 5,869,681 A | 2/1999 | Muller et al. |
| 6,040,331 A | 3/2000 | Yamamoto et al. |
| 6,218,418 B1 | 4/2001 | Pevarello et al. |
| 6,506,747 B1 | 1/2003 | Betageri et al. |
| 6,548,525 B2 | 4/2003 | Galemmo, Jr. et al. |
| 6,720,427 B2 | 4/2004 | Sanner et al. |
| 6,878,196 B2 | 4/2005 | Harada et al. |
| 6,916,927 B2 | 7/2005 | Bunnage et al. |
| 6,965,032 B2 | 11/2005 | Freudenberger et al. |
| 7,192,906 B2 | 3/2007 | Hirohara et al. |
| 7,196,104 B2 | 3/2007 | Askew, Jr. et al. |
| 7,319,108 B2 | 1/2008 | Schwink et al. |
| 7,774,978 B2 | 8/2010 | Ding et al. |
| 7,803,832 B2 | 9/2010 | Critcher et al. |
| 7,910,606 B2 | 3/2011 | Nazare et al. |
| 7,923,573 B2 | 4/2011 | Tamaki et al. |
| 8,163,756 B2 | 4/2012 | Flynn et al. |
| 8,222,280 B2 | 7/2012 | Liu et al. |
| 8,901,153 B2 | 12/2014 | Buysse et al. |
| 9,024,031 B1 | 5/2015 | Yang et al. |
| 9,029,554 B1 | 5/2015 | Yang et al. |
| 9,029,555 B1 | 5/2015 | Li et al. |
| 9,029,556 B1 | 5/2015 | Yang et al. |
| 9,044,017 B2 | 6/2015 | Yang et al. |
| 9,085,552 B1 | 7/2015 | Li et al. |
| 9,085,564 B2 | 7/2015 | Yang et al. |

(Continued)

FOREIGN PATENT DOCUMENTS

EP    0097323    1/1984
EP    0190457    8/1986

(Continued)

OTHER PUBLICATIONS

Kempe et al., "Responsive Glyco-poly(2-oxaoline)s: Synthesis, Cloud Point Tuning, and Lectin Binding," Biomacromolecules 2011, vol. 12, pp. 2591-2600.

(Continued)

*Primary Examiner* — Patricia L Morris

(74) *Attorney, Agent, or Firm* — Carl D. Corvin; Barnes & Thornburg LLP

(57) ABSTRACT

The present application provides processes for making pesticidal compounds and compounds useful both as pesticides and in the making of pesticidal compounds.

1 Claim, No Drawings

(56) References Cited

U.S. PATENT DOCUMENTS

| | | |
|---|---|---|
| 9,102,654 B2 | 8/2015 | Yang et al. |
| 9,102,655 B2 | 8/2015 | Yang et al. |
| 9,108,932 B2 | 8/2015 | Ross et al. |
| 9,108,946 B2 | 8/2015 | Yang et al. |
| 9,115,115 B1 | 8/2015 | Yang et al. |
| 9,126,974 B2 | 9/2015 | Yang et al. |
| 9,156,813 B1 | 10/2015 | Li et al. |
| 9,174,962 B2 | 11/2015 | Yang et al. |
| 9,199,942 B2 | 12/2015 | Yang et al. |
| 9,199,964 B1 | 12/2015 | Yang et al. |
| 9,249,122 B1 | 2/2016 | Yang et al. |
| 9,255,081 B1 | 2/2016 | Li et al. |
| 9,255,082 B2 | 2/2016 | Yang et al. |
| 9,255,083 B2 | 2/2016 | Yang et al. |
| 9,260,396 B2 | 2/2016 | Yang et al. |
| 9,371,310 B2 | 6/2016 | Yang et al. |
| 9,414,594 B2 | 8/2016 | Yang et al. |
| 9,422,265 B2 | 8/2016 | Li et al. |
| 2002/0013326 A1 | 1/2002 | Tiebes et al. |
| 2003/0153464 A1 | 8/2003 | Nakamura et al. |
| 2003/0213405 A1 | 11/2003 | Harada et al. |
| 2004/0043904 A1 | 3/2004 | Yamaguchi et al. |
| 2004/0082629 A1 | 4/2004 | Iwataki et al. |
| 2005/0038059 A1 | 2/2005 | Mueller et al. |
| 2005/0176710 A1 | 8/2005 | Schwink et al. |
| 2006/0135778 A1 | 6/2006 | Schnatterer et al. |
| 2006/0160857 A1 | 7/2006 | Buettelmann et al. |
| 2006/0160875 A1 | 7/2006 | Gaines et al. |
| 2006/0167020 A1 | 7/2006 | Dickerson et al. |
| 2006/0287365 A1 | 12/2006 | Billen et al. |
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2008/0004301 A1 | 1/2008 | Tamaki et al. |
| 2008/0027046 A1 | 1/2008 | Annan et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0275592 A1 | 11/2009 | Zeng et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wada et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fublein et al. |
| 2012/0053146 A1 | 3/2012 | Parker et al. |
| 2012/0094837 A1 | 4/2012 | Muhlthau et al. |
| 2012/0095023 A1 | 4/2012 | Bretschneider et al. |
| 2012/0101294 A1 | 4/2012 | Hirota et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2014/0162874 A1 | 6/2014 | Yap et al. |
| 2016/0152593 A1 | 6/2016 | Li et al. |

FOREIGN PATENT DOCUMENTS

| | | |
|---|---|---|
| EP | 0205024 | 12/1986 |
| EP | 0248315 | 12/1987 |
| EP | 0425948 | 5/1991 |
| EP | 1273582 | 1/2003 |
| EP | 1321463 | 6/2003 |
| EP | 1329160 | 7/2003 |
| JP | 1987-153273 | 7/1987 |
| JP | 1988-174905 | 7/1988 |
| JP | 1989-226815 | 9/1989 |
| JP | 2003-212864 | 7/2003 |
| JP | 2004-051628 | 2/2004 |
| JP | 2004-292703 | 10/2004 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 94/13644 | 6/1994 |
| WO | 97/36897 | 10/1997 |
| WO | 98/49166 | 11/1998 |
| WO | 00/35919 | 6/2000 |
| WO | 01/34127 | 5/2001 |
| WO | 01/90078 | 11/2001 |
| WO | 02/083111 | 10/2002 |
| WO | 03/008405 | 1/2003 |
| WO | 03/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |
| WO | 2006/103045 | 10/2006 |
| WO | 2007/005838 | 1/2007 |
| WO | 2008/090382 | 7/2007 |
| WO | 2007/087427 | 8/2007 |
| WO | 2007/098826 | 9/2007 |
| WO | 2008/005457 | 1/2008 |
| WO | 2008/079277 | 7/2008 |
| WO | 2011/045224 | 10/2009 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045240 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011/134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2010/035011 | 3/2012 |
| WO | 2012/052412 | 4/2012 |
| WO | 2012/061290 | 5/2012 |
| WO | 2012/070114 | 5/2012 |
| WO | 2012/102387 | 8/2012 |
| WO | 2012/108511 | 8/2012 |
| WO | 2012/147107 | 11/2012 |

(56) References Cited

FOREIGN PATENT DOCUMENTS

| WO | 2012/168361 | 12/2012 |
|---|---|---|
| WO | 2013/000931 | 1/2013 |
| WO | 2013/010946 | 1/2013 |
| WO | 2013/010947 | 1/2013 |
| WO | 2013/062980 | 5/2013 |
| WO | 2013/062981 | 5/2013 |
| WO | 2013/064324 | 5/2013 |
| WO | 2013/156431 | 10/2013 |
| WO | 2013/156433 | 10/2013 |

OTHER PUBLICATIONS

Fields et al., "Preparation of Trifluoromethyl-Pyrazoles and -Pyrazolines by the Reaction of 2,2,2-Trifluorodiazoethane with Carbon-Carbon Multiple Bonds," Journal of Fluorine Chemistry, 1979, vol. 13, pp. 147-158.
Bradbury et al., "Enzyme-catalysed peptide amidation," Eur. J. Biochem. 1987, vol. 169, pp. 579-584.
International Search Report and Written Opinion for PCT/US2014/061005 mailed Dec. 16, 2014.
International Search Report and Written Opinion for PCT/US2014/061006 mailed Dec. 8, 2014.
International Search Report and Written Opinion for PCT/US2014/061007 mailed Dec. 31, 2014.
International Search Report and Written Opinion for PCT/US2014/061009 mailed Dec. 8, 2014.
International Search Report and Written Opinion for PCT/US2014/061010 mailed Dec. 15, 2014.
International Search Report and Written Opinion for PCT/US2014/061012 mailed Dec. 15, 2014.
International Search Report and Written Opinion for PCT/US2014/061014 mailed Dec. 15, 2014.
International Search Report and Written Opinion for PCT/US2014/061016 mailed Dec. 15, 2014.
International Search Report and Written Opinion for PCT/US2014/061022 mailed Dec. 29, 2014.
International Search Report and Written Opinion for PCT/US2014/061023 mailed Dec. 15, 2014.
International Search Report and Written Opinion for PCT/US2014/061024 mailed Dec. 15, 2014.
International Search Report and Written Opinion for PCT/US2014/061027 mailed Dec. 15, 2014.
International Search Report and Written Opinion for PCT/US2014/061029 mailed Dec. 15, 2014.
International Search Report and Written Opinion for PCT/US2014/061030 mailed Dec. 15, 2014.
International Search Report and Written Opinion for PCT/US2013/029615 mailed May 8, 2013.
Ameduri, B. et al., "Synthesis and polymerization of fluorinated monomers bearing a reactive lateral group Part 4. Preparation of functional perfluorovinyl monomers by radical addition of functional mercaptans to 1,1,2-trifluoro-1,4-pentadiene." J. Fluorine Chemistry, 92, 77-84 (1998).
International Preliminary Report on Patentability for PCT/US2011/058578 mailed Dec. 21, 2012.
International Search Report and Written Opinion for PCT/US2011/058578 mailed Apr. 5, 2012.
Kadam, S.S. et al., "Tautomerism of Substituted Pyrazolo[4,3-c]pyrazoles." Eur. J. Chem., 6811-6822 (2013).
Gorelik; Zhumai Organicheskol khimi, 1980 (16), 1322, Abstract, Chemical Abstracts, Accession No. 1980;620652.
National Center for Biotechnology Information, PubChem Compound Database; CID=17132489,https://pubchem.ncbi.nlm.nih.gov/compound/17132489, create date Nov. 13, 2007.
Frigola; European Journal of Medicinal Chemistry 1989, 435-445.

PROCESSES FOR THE PREPARATION OF PESTICIDAL COMPOUNDS

CROSS REFERENCE TO RELATED APPLICATIONS

This Application is a divisional of U.S. application Ser. No. 14/989,269 filed on Jan. 6, 2016, is a divisional of U.S. application Ser. No. 14/718,621 filed on May 21, 2015, which is a divisional of U.S. application Ser. No. 14/517,595 filed on Oct. 17, 2014, which claims the benefit of the following U.S. Provisional Patent Applications: Ser. No. 62/034,456, filed Aug. 7, 2014; Ser. No. 62/001,925, filed May 22, 2014; and Ser. No. 61/892,124, filed Oct. 17, 2013, the entire disclosures of these applications are hereby expressly incorporated by reference into this Application.

TECHNICAL FIELD

This application relates to efficient and economical synthetic chemical processes for the preparation of pesticidal thioethers and pesticidal sulfoxides. Further, the present application relates to certain novel compounds necessary for their synthesis. It would be advantageous to produce pesticidal thioethers and pesticidal sulfoxides efficiently and in high yield from commercially available starting materials.

DETAILED DESCRIPTION

The following definitions apply to the terms as used throughout this specification, unless otherwise limited in specific instances.

As used herein, the term "alkyl" denotes branched or unbranched hydrocarbon chains.

As used herein, the term "alkynyl" denotes branched or unbranched hydrocarbon chains having at least one C≡C.

Unless otherwise indicated, the term "cycloalkyl" as employed herein alone is a saturated cyclic hydrocarbon group, such as cyclopropyl, cyclobutyl, cyclopentyl, cyclohexyl.

The term "thio" as used herein as part of another group refers to a sulfur atom serving as a linker between two groups.

The term "halogen" or "halo" as used herein alone or as part of another group refers to chlorine, bromine, fluorine, and iodine.

The compounds and process of the present application are described in detail below in scheme 1.

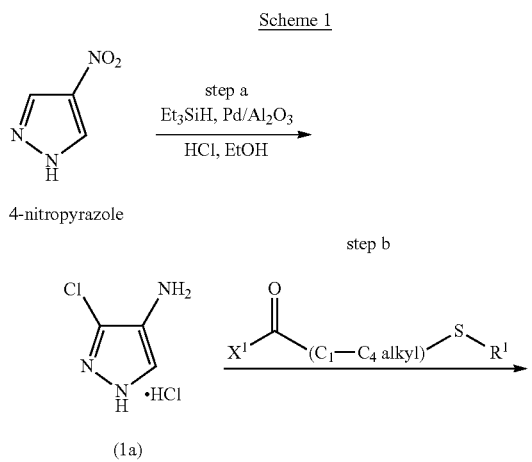

In step a of Scheme 1,4-nitropyrazole is halogenated and reduced to yield 3-chloro-1H-pyrazol-4-amine hydrochloride (1a). The halogenation occurs at the 3-carbon through the use of concentrated (37 weight percent) hydrochloric acid. The reduction occurs with triethylsilane and palladium on alumina (preferably about 1 to 10 weight percent palladium on alumina, more preferably about 5 weight percent). This reaction may be conducted at a temperature from about 10° C. to about 20° C. This reaction may be conducted in a polar protic solvent, such as methanol or ethanol, preferably ethanol. It was surprisingly discovered, that by utilizing about 1 to about 4 equivalents, preferably, about 2.5 equivalents to about 3.5 equivalents of triethylsilane in this step, while conducting the reaction between about 0° C. to about 40° C., preferably 10° C. and about 20° C., gives about a 10:1 molar ratio of the desired halogenated product 3-chloro-1H-pyrazol-4-amine hydrochloride (1a)

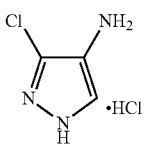

(Ia)

versus the undesired product

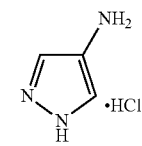

1H-pyrazol-4-amine
hydrochloride

In step b of Scheme 1,3-chloro-1H-pyrazol-4-amine hydrochloride (1a) is reacted with an activated carbonyl thioether, indicated as $X^1C(=O)C_1$-$C_4$-alkyl-S—$R^1$, to produce pesticidal thioether (3a). $R^1$ is selected from the group consisting of $C_1$-$C_4$-haloalkyl and $C_1$-$C_4$-alkyl-$C_3$-$C_6$-halocycloalkyl, preferably, $R^1$ is selected from $CH_2CH_2CF_3$ or $CH_2$(2,2-difluorocyclopropyl). $X^1$ is selected from Cl, $OC(=O)C_1$-$C_4$ alkyl, or a group $X^1$ that forms an activated carboxylic acid. When $X^1$ is Cl or $OC(=O)C_1$-$C_4$ alkyl, the reaction may be conducted in the presence of a base preferably, sodium bicarbonate at temperatures from about −10° C. to about 40° C. to yield pesticidal thioether (3a). The reaction may be conducted in a solvent mixture such as tetrahydrofuran and water. It has been surprisingly discovered the thioether (3a) produced by this synthetic route is only monoacylated due to the presence of the chloro group at the 3-position of the pyrazole ring. Described herein is a comparative example without a halogen at the 3-position that yielded the double acylated product (see "CE-1"). Further, comparative example with a bromo group at the 3-position afforded the product in a surprisingly low yield compared to the yield with the chloro group (see "CE-2").

Alternatively, the reaction may be accomplished when $X^1C(=O)C_1$-$C_4$-alkyl-S—$R^1$ is an activated carboxylic acid activated by such reagents as 2,4,6-tripropyl-trioxatriphosphinane-2,4,-trioxide, carbonyldiimidazole, dicyclohexylcarbodiimide or 1-ethyl-3-(3-dimethylaminopropyl)-carbodiimide at temperatures from about 0° C. to about 80° C.; this reaction may also be facilitated with uronium or phosphonium activating groups such as O-(7-azabenzotriazol-1-yl)-N,N,N',N'-tetramethyluronium hexafluorophosphate or benzotriazol-1-yl-oxytripyrrolidinophosphonium hexafluorophosphate, in the presence of an amine base such as diisopropylethylamine or triethylamine in a polar aprotic solvent such as N,N-dimethylformamide, tetrahydrofuran, or dichloromethane, at temperatures from about −10° C. to about 30° C. to form pesticidal thioether (3a). Activated carbonyl thioethers, may be prepared from $X^1C(=O)C_1$-$C_4$-alkyl-S—$R^1$, wherein $X^1$ is OH, which may be prepared by reacting the corresponding ester thioether, indicated as $X^1C(=O)C_1$-$C_4$-alkyl-S—$R^1$ wherein $X^1$ is $OC_1$-$C_4$-alkyl, with a metal hydroxide such as lithium hydroxide in a polar solvent such as methanol or tetrahydrofuran. Alternatively, $X^1C(=O)C_1$-$C_4$-alkyl-S—$R^1$, wherein $X^1$ is OH or $OC_1$-$C_4$-alkyl may be prepared by the photochemical free-radical coupling of 3-mercaptopropionic acid and esters thereof with 3,3,3-trifluoropropene in the presence of 2,2-dimethoxy-2-phenylacetophenone initiator and long wavelength UV light in an inert organic solvent. While stoichiometric amounts of 3-mercaptopropionic acid or esters thereof and 3,3,3-trifluoropropene are required, because of its low boiling point, excess 3,3,3-trifluoropropene is usually employed to compensate for routine losses. From about 1 to about 10 mole percent initiator, 2,2-dimethoxy-2-phenylacetophenone, is typically used, with about 5 mole percent being preferred. Long wavelength UV light is sometimes called "black light" and ranges from about 400 to about 365 nanometers. The photochemical coupling is conducted in an inert organic solvent. Typical inert organic solvents must remain liquid to about −50° C., must remain relatively inert to the free radical conditions and must dissolve the reactants at reaction temperatures. Preferred inert organic solvents are aromatic and aliphatic hydrocarbons like toluene. The temperature at which the reaction is conducted is not critical but usually is from about −50° C. to about 35° C. Initially, it is important to keep the temperature below the boiling point of 3,3,3-trifluoropropene, i.e., about −18 to about −16° C. In a typical reaction, the inert organic solvent is cooled to less than about −50° C. and the 3,3,3-trifluoropropene is bubbled into the solvent. The 3-mercaptopropionic acid or esters thereof and 2,2-dimethoxy-2-phenylacetophenone are added and a long wave function (366 nm) UVP lamp (4 watt) is turned on. After sufficient conversion of 3-mercapto-propionic acid or esters thereof, the light is turned off and the solvent removed.

3-((3,3,3-Trifluoropropyl)thio)propanoic acid may also be prepared by the low temperature free-radical initiated coupling of 3-mercaptopropionic acid with 3,3,3-trifluoropropene in the presence of 2,2'-azobis(4-methoxy-2,4-dimethyl) valeronitrile (V-70) initiator at temperatures of about −50° C. to about 40° C. in an inert organic solvent. While stoichiometric amounts of 3-mercaptopropionic acid and 3,3,3-trifluoropropene are required, because of its low boiling point, excess 3,3,3-trifluoropropene is usually employed to compensate for routine losses. From about 1 to about 10 mole percent initiator, V-70, is typically used, with about 5 mole percent being preferred. The low temperature free-radical initiated coupling is conducted in an inert organic solvent. Typical inert organic solvents must remain liquid to about −50° C., must remain relatively inert to the free radical conditions and must dissolve the reactants at reaction temperatures. Preferred inert organic solvents are toluene, ethyl acetate, and methanol. The temperature at which the reaction is conducted from about −50° C. to about 40° C. The solution is cooled to less than about −50° C. and the 3,3,3-trifluoropropene is transferred into the reaction mixture. After stirring at room temperature for 24 hours, the reaction mixture is heated to about 50° C. for about 1 hour to decompose any remaining V-70 initiator followed by cooling and solvent removal.

In step c of Scheme 1, thioether (3a) is reacted with a halopyridine, preferably, 3-bromopyridine in the presence of a copper salt, (such as copper(I) chloride, copper(II) chloride, and copper(I) iodide), a base such as potassium phosphate, and potassium carbonate, preferably potassium carbonate, and N,N'-dimethylethane-1,2-diamine to yield pesticidal thioether (3b). This synthetic method is simpler and reduces the costs of starting materials over known heteroarylation methods. The process may be conducted in a polar solvent, such as, acetonitrile, dioxane, or N,N-dimethylformamide at a temperature between about 50° C. and about 110° C., preferably between about 70° C. and about 90° C. It is preferred that the reaction mixture is stirred with heating for between 2 hours and 24 hours.

In step d of Scheme 1, pesticidal thioether (3b) is alkylated preferably with a $R^2$—$X^2$ to yield pesticidal thioether (3c), wherein $X^2$ is a leaving group. The leaving group may be selected from halo, mesylate, or tosylate. $R^2$ is selected from $C_1$-$C_4$-alkyl, $C_2$-$C_4$-alkynyl, preferably, methyl, ethyl, and propargyl. $R^2$—$X^2$ may be selected from methyl iodide, ethyl bromide, ethyl iodide, propargyl chloride, propargyl bromide, ethyl mesylate, propargyl mesylate, ethyl tosylate, and propargyl tosylate. The alkylation is conducted in the presence of an inorganic base, preferably, metal carbonates such as cesium carbonate, metal hydroxides, metal phosphates, metal hydrides, conducted in the presence of a polar solvent, preferably N,N-dimethylformamide at temperatures from about 0° C. to about 80° C.

Alternatively, in step d of Scheme 1, the alkylation of pesticidal thioether (3b) may be conducted in the presence of a base such as sodium hydride, in the presence of a polar aprotic solvent, such as N,N-dimethylformamide, tetrahydrofuran, hexamethylphosphoramide, dimethylsulfoxide, N-methyl-2-pyrrolidinone, and sulfolane, at temperatures from about 0° C. to about 30° C. It has been unexpectedly discovered that the use of sulfolane as solvent promotes the alkylation reaction over the competitive retry-Michael-type elimination of the $C_1$-$C_4$-alkyl-S—$R^1$ unit (see "CE-3"). It has been discovered that the catalytic use of an iodide additive, such as potassium iodide or tetrabutylammonium iodide decreases the time necessary for the reaction to occur to about 24 hours. It was also discovered that heating the reaction at about 50° C. to about 70° C. in a sealed reactor (to prevent loss of ethyl bromide) decreases the reaction time to about 24 hours.

In step e of Scheme 1 thioether (3c) is oxidized with hydrogen peroxide ($H_2O_2$) in methanol to yield the desired pesticidal sulfoxides (3d).

EXAMPLES

The following examples are presented to better illustrate the processes of the present application.

Example 1 3-chloro-1H-pyrazol-4-amine hydrochloride (1a)

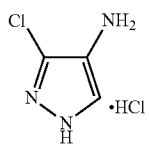

A 1000-mL, multi-neck cylindrical jacketed reactor, fitted with a mechanical stirrer, temperature probe and nitrogen inlet, was charged with 4-nitropyrazole (50.0 g, 429 mmol) and palladium on alumina (5 wt %, 2.5 g). Ethanol (150 mL) was added, followed by a slow addition of concentrated hydrochloric acid (37 wt %, 180 mL). The reaction was cooled to 15° C., and triethylsilane (171 mL, 1072 mmol) was added slowly via addition funnel over 1 hour, while maintaining the internal temperature at 15° C. The reaction was stirred at 15° C. for 72 hours, after which the reaction mixture was filtered through a Celite® pad and the pad was rinsed with warm ethanol (40° C., 2×100 mL). The combined filtrates were separated and the aqueous layer (bottom layer) was concentrated to ~100 mL. Acetonitrile (200 mL) was added and the resulting suspension was stirred at 20° C. for 1 hour and filtered. The filter cake was rinsed with acetonitrile (2×100 mL) and dried under vacuum at 20° C. to afford a white solid (~10:1 mixture of 1a and 1H-pyrazol-4-amine, 65.5 g, 99%): $^1$H NMR (400 MHz, DMSO-$d_6$) δ 10.52 (bs, 3H), 8.03 (s, 1H); EIMS m/z 117 ([M]$^+$).

Example 2 N-(3-chloro-1H-pyraxol-4-yl)-3-((3,3,3,trifluoropropyl)thio)propanamide (Compound 2.3)

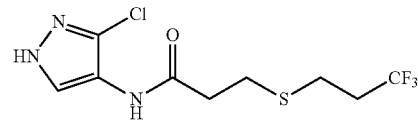 [SMILES: O=C(CCSCCC(F)(F)F)Nc1c[nH]nc1Cl]

A 100 mL, 3-neck flask was charged with 3-chloro-1H-pyrazol-4-amine hydrochloride (5.00 g, 32.5 mmol), tetrahydrofuran (25 mL) and water (25 mL). The resulting suspension was cooled to 5° C. and sodium bicarbonate (10.9 g, 130 mmol) was added, followed by dropwise addition of 3-((3,3,3,-trifluoropropyl)thio)propanoyl chloride (7.52 g, 34.1 mmol) at <5° C. The reaction was stirred at <10° C. for 1 hour, at which point thin layer chromatography analysis (Eluent: 1:1 ethyl acetate/hexane) indicated the starting material was consumed and the desired product was formed. The reaction mixture was diluted with ethyl acetate (25 mL) and water (25 mL). The layers were separated and the aqueous layer was extracted with ethyl acetate (3×25 mL). The organic layers were combined and concentrated to dryness. The residue was suspended in 2:1 methyl tert-butylether/heptanes (30 mL), stirred for 1 hour and filtered. The solid was rinsed with 2:1 methyl tert-butylether/heptanes (20 mL) and further dried under vacuum at room temperature (about 22° C.) to afford a white solid (7.80 g, 80%): mp 83-85° C.; $^1$H NMR (400 MHz, DMSO-$d_6$) δ 12.90 (s, 1H), 9.59 (s, 1H), 8.02 (s, 1H), 2.82 (t, J=7.2 Hz, 2H), 2.76-2.69 (m, 2H), 2.66 (t, J=7.1 Hz, 2H), 2.62-2.48 (m, 2H); $^{13}$C NMR (101 MHz, DMSO-$d_6$) δ 168.97, 129.95, 126.60 (q, J=277.4 Hz), 123.42, 116.60, 35.23, 33.45 (q, J=27.3 Hz), 26.85, 23.03 (q, J=3.4 Hz); EIMS m/z 301 ([M]$^+$).

Example 3 3-((3,3,3-trifluoropropyl)thio)propanoic acid

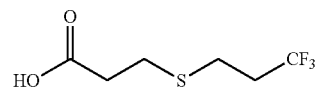

A 100 mL, 3-neck round bottom flask was charged with 3-bromopropanoic acid (500 mg, 3.27 mmol) and methanol (10 mL), potassium hydroxide (403 mg, 7.19 mmol) was added, followed by 3,3,3-trifluoropropane-1-thiol (468 mg, 160 mmol). The mixture was heated at 50° C. for 4 hours, after which it was acidified with 2 N hydrochloric acid and extracted with methyl tert-butylether (2×10 mL). The organic layer was concentrated to dryness to afford a light yellow oil (580 mg, 88%): $^1$H NMR (400 MHz, CDCl$_3$) δ 2.83 (td, J=7.1, 0.9 Hz, 2H), 2.78-2.64 (m, 4H), 2.48-2.32 (m, 2H).

Alternate Synthetic Route to 3-((3,3,3-trifluoropropyl)thio)propanoic Acid:

A 100 mL stainless steel Parr reactor was charged with azobisisobutyronitrile (0.231 g, 1.41 mmol), toluene (45 mL), 3-mercaptopropionic acid (3.40 g, 32.0 mmol), and octanophenone (526.2 mg) as an internal standard and was purged and pressure checked with nitrogen. The reactor was cooled with dry ice and the 3,3,3-trifluoropropene (3.1 g, 32.3 mmol) was condensed into the reactor. The ice bath was removed and the reactor heated to 60° C. and stirred for 27 hours. The internal yield of the reaction was determined to be 80% by use of the octanophenone internal standard. The pressure was released and the crude mixture removed from the reactor. The mixture was concentrated by rotary evaporation and 50 mL of 10% sodium hydroxide was added. The solution was washed with methyl tert-butylether (50 mL) then acidified to pH ~1 with 6 N hydrochloric acid. The product was extracted with 100 mL methyl tert-butylether, dried over magnesium sulfate, filtered, and concentrated to give the crude titled compound as an oil (5.34 g, 26.4 mmol, 83%, 87.5 area % on GC): $^1$H NMR (400 MHz, CDCl$_3$) δ 2.83 (td, J=7.1, 0.9 Hz, 2H), 2.76-2.64 (m, 4H), 2.47-2.30 (m, 2H); $^{13}$C NMR (101 MHz, CDCl$_3$) δ 177.68, 125.91 (q, J=277.1 Hz), 34.58 (q, J=28.8 Hz), 34.39, 26.63, 24.09 (q, J=3.3 Hz); $^{19}$F NMR (376 MHz, CDCl$_3$) δ −66.49.

Alternate Synthetic Route to 3-((3,3,3-trifluoropropyl)thio)propanoic Acid:

A 250 mL three-neck round bottomed flask was charged with toluene (81 mL) and cooled to <−50° C. with a dry ice/acetone bath. 3,3,3-Trifluoropropene (10.28 g, 107.0 mmol) was bubbled into the solvent and the ice bath was removed. 3-Mercaptopropionic acid (9.200 g, 86.70 mmol) and 2,2-dimethoxy-2-phenylacetophenone (1.070 g, 4.170 mmol) were added and the long wave light (366 nm, 4 watt UVP lamp) was turned on (Starting temperature: −24° C.). The reaction reached a temperature of 27.5° C. due to heat from the lamp. The reaction was stirred under the black light on for 4 hours. After 4 hours the black light was turned off and the reaction concentrated by rotary evaporation (41° C., 6 mm Hg) giving a pale yellow oil (18.09 g, 51:1 linear:branched isomer, 90 wt % linear isomer by GC internal standard assay, 16.26 g active, 93%). The crude material was dissolved in 10% sodium hydroxide w/w (37.35 g) and was washed with toluene (30 mL) to remove non-polar impurities. The aqueous layer was acidified to pH ~2-3 with hydrochloric acid (2 N, 47.81 g) and was extracted with toluene (50 mL). The organic layer was washed with water (40 mL) and dried over magnesium sulfate, filtered, and concentrated by rotary evaporation giving a pale yellow oil (14.15 g, 34:1 linear:branched isomer, 94 wt % linear isomer by GC internal standard assay, 13.26 g active, 76%).

Alternative Synthesis of 3-((3,3,3-trifluoropropyl)thio)propanoic Acid:

A 100 mL stainless steel Parr reactor was charged with 3-mercaptopropionic acid (3.67 g, 34.6 mmol), toluene (30.26 g), and 2,2'-azobis(4-methoxy-2,4-dimethyl) valeronitrile (V-70, 0.543 g, 1.76 mmol) and the reactor was cooled with a dry ice/acetone bath, purged with nitrogen, and pressure checked. 3,3,3-Trifluoropropene (3.20 g, 33.3 mmol) was added via transfer cylinder and the reaction was allowed to warm to 20° C. After 24 hours, the reaction was heated to 50° C. for 1 hour to decompose any remaining V-70 initiator. The reaction was allowed to cool to room temperature. The solution was concentrated by rotary evaporation to provide the title compound (6.80 g, 77.5 wt % linear isomer by GC internal standard assay, 5.27 g active, 76%, 200:1 linear:branched by GC, 40:1 linear:branched by fluorine NMR)

Example 4
methyl-3-((3,3,3-trifluoropropyl)thio)propionate
(Compound 7.1)

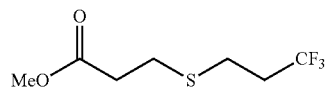

A 100 mL stainless steel Parr reactor was charged with azobisisobutyronitrile (0.465 g, 2.83 mmol), toluene (60 mL) and methyl-3-mercaptopropionate (7.40 g, 61.6 mmol) and was purged and pressure checked with nitrogen. The reactor was cooled with dry ice and the 3,3,3-trifluoropropopene (5.70 g, 59.3 mmol) was condensed into the reactor. The ice bath was removed and the reactor heated to 60° C. and stirred to 24 hours. The heat was turned off and the reaction left at room temperature overnight. The mixture was removed from the reactor and concentrated to a yellow liquid. The liquid was distilled by vacuum distillation (2 Torr, 85° C.) and three fractions were collected: fraction 1 (1.3 g, 6.01 mmol, 10%, 70.9 area % by GC), fraction 2 (3.7 g, 17.1 mmol, 29%, 87 area % by GC), and fraction 3 (4.9 g, 22.7 mmol, 38%, 90.6 area % by GC): $^1$H NMR (400 MHz, CDCl$_3$) δ 3.71 (s, 3H), 2.82, (td, J=7.3, 0.7 Hz, 2H), 2.75-2.68 (m, 2H), 2.63 (td, J=7.2, 0.6 Hz, 2H), 2.47-2.31 (m, 2H); $^{13}$C NMR (101 MHz, CDCl$_3$) δ 172.04, 125.93 (q, J=277.2 Hz), 51.86, 34.68 (q, J=28.6 Hz), 34.39, 27.06, 24.11 (q, J=3.3 Hz); $^{19}$F NMR (376 MHz, CDCl$_3$) δ −66.53.

Alternate Synthetic Route to methyl-3-((3,3,3-trifluoropropyl)thio)propionate:

A 500 mL three-neck round bottomed flask was charged with toluene (200 mL) and cooled to <−50° C. with a dry ice/acetone bath. 3,3,3-Trifluoropropene (21.8 g, 227 mmol) was condensed into the reaction by bubbling the gas through the cooled solvent and the ice bath was removed. Methyl 3-mercaptopropionate (26.8 g, 223 mmol) and 2,2-dimethoxy-2-phenylacetophenone (2.72 g, 10.61 mmol) were added and a UVP lamp (4 watt) that was placed within 2 centimeters of the glass wall was turned on to the long wave function (366 nanometers). The reaction reached 35° C. due to heat from the lamp. After 4 hours, all of the trifluoropropene was either consumed or boiled out of the reaction. The light was turned off and the reaction stirred at room temperature overnight. After 22 hours, more trifluoropropene (3.1 g) was bubbled through the mixture at room temperature and the light was turned on for an additional 2 hours. The reaction had converted 93% so no more trifluoropropene was added. The light was turned off and the mixture concentrated on the rotovap (40° C., 20 torr) giving a yellow liquid (45.7 g, 21.3:1 linear: branched isomer, 75 wt % pure linear isomer determined by a GC internal standard assay, 34.3 g active, 71% in pot yield).

Alternate Synthetic Route to methyl-3-((3,3,3-trifluoropropyl)thio)propionate:

A 100 mL stainless steel Parr reactor was charged with methyl 3-mercaptopropionate (4.15 g, 34.5 mmol), toluene (30.3 g), and 2,2'-azobis(4-methoxy-2,4-dimethyl) valeronitrile (V-70, 0.531 g, 1.72 mmol) and the reactor was cooled with a dry ice/acetone bath, purged with nitrogen, and pressure checked. 3,3,3-Trifluoropropene (3.40 g, 35.4 mmol) was added via transfer cylinder and the reaction was allowed to warm to 20° C. After 23 hours the reaction was heated to 50° C. for 1 hour to decompose any remaining V-70 initiator. The reaction was allowed to cool to room temperature. The solution was concentrated to provide the title compound (7.01 g, 66%, 70.3 wt % linear isomer by GC internal standard assay, 4.93 g active, 66%, 24:1 linear:branched by GC, 18:1 linear:branched by fluorine NMR).

Example 5 N-(3-chloro-1-(pyridin-3-yl)-1H-pyrazol-4-yl)-3(3,3,3-trifluoropropyl)thio)propanamide (Compound 5.3)

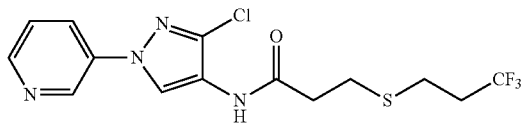 [SMILES: O=C(CCSCCC(F)(F)F)Nc1cn(-c2cccnc2)nc1Cl]

A 100 mL, 3-neck round bottom flask was charged with copper(I) iodide (0.343 g, 1.80 mmol), acetonitrile (50 mL), N,N'-dimethylethane-1,2-diamine (0.318 g, 3.61 mmol), N-(3-chloro-1H-pyrazol-4-yl)-3-((3,3,3-trifluoropropylthio)propanamide (2.72 g, 9.02 mmol), $K_2CO_3$ (2.49 g, 18.0 mmol) and 3-bromopyridine (1.71 g, 10.8 mmol). The mixture was purged with nitrogen three times and heated to 80° C. for 4 hours, at which point thin layer chromatography analysis (Eluent: ethyl acetate) indicated that only a trace of starting material remained. The mixture was filtered through a Celite® pad and the pad was rinsed with acetonitrile (20 mL). The filtrates were concentrated to dryness and the residue was purified by flash column chromatography using 0-100% ethyl acetate/hexanes as eluent. The fractions containing pure product were concentrated to dryness and further dried under vacuum to afford a white solid (1.82 g, 53%): mp 99-102° C.; $^1$H NMR (400 MHz, DMSO-$d_6$) δ 9.92 (s, 1H), 9.05 (d, J=2.7 Hz, 1H), 8.86 (s, 1H), 8.54 (dd, J=4.5, 1.4 Hz, 1H), 8.21 (ddd, J=8.4, 2.7, 1.4 Hz, 1H), 7.54 (dd, J=8.4, 4.7 Hz, 1H), 2.86 (t, J=7.3 Hz, 2H), 2.74 (td, J=6.5, 5.6, 4.2 Hz, 4H), 2.59 (ddd, J=11.7, 9.7, 7.4 Hz, 2H); $^{13}$C NMR (101 MHz, DMSO-$d_6$) δ 169.32, 147.49, 139.44, 135.47, 133.40, 126.60 (q, J=296 Hz), 125.49, 124.23, 122.30, 120.00, 35.18, 33.42 (q, J=27.2 Hz), 26.77, 23.05 (q, J=3.3 Hz); EIMS m/z 378 ([M]$^+$).

Example 6 N-(3-chloro-1-(pyridin-3-yl)-1H-pyrazol-4-yl)-N-ethyl-3-((3,3,3-trifluoropropyl)thio)propanamide (Compound 6.3)

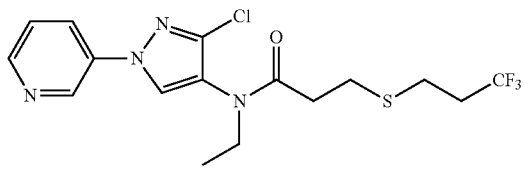 [SMILES: CCN(C(=O)CCSCCC(F)(F)F)c1cn(-c2cccnc2)nc1Cl]

A 100 mL, 3-neck round bottom flask, equipped with mechanical stirrer, temperature probe and nitrogen inlet was charged with cesium carbonate (654 mg, 2.01 mmol), N-(3-chloro-1-(pyridin-3-yl)-1H-pyrazol-4-yl)-3-((3,3,3-trifluoropropypthio)propanamide (380 mg, 1.00 mmol) and N,N-dimethylformamide, (5 mL). Iodoethane (0.0890 mL, 1.10 mmol) was added dropwise. The reaction was stirred at 40° C. for 2 hours, at which point thin layer chromatography analysis (Eluent: ethyl acetate) indicated that only a trace of starting material remained. The reaction mixture was cooled to 20° C. and water (20 mL) was added. It was extracted with ethyl acetate (2×20 mL) and the combined organic layers were concentrated to dryness at <40° C. The residue was purified by flash column chromatography using 0-100% ethyl acetate/hexane as eluent. The fractions containing pure product were concentrated to dryness to afford a colorless oil (270 mg, 66%): $^1$H NMR (400 MHz, DMSO-$d_6$) δ 9.11 (d, J=2.7 Hz, 1H), 8.97 (s, 1H), 8.60 (dd, J=4.8, 1.4 Hz, 1H), 8.24 (ddd, J=8.4, 2.8, 1.4 Hz, 1H), 7.60 (ddd, J=8.4, 4.7, 0.8 Hz, 1H), 3.62 (q, J=7.1 Hz, 2H), 2.75 (t, J=7.0 Hz, 2H), 2.66-2.57 (m, 2H), 2.57-2.44 (m, 2H), 2.41 (t, J=7.0 Hz, 2H), 1.08 (t, J=7.1 Hz, 3H); EIMS: m/z 406 ([M]$^+$).

Alternate Synthetic Route to N-(3-chloro-1-(pyridin-3-yl)-1H-pyrazol-4-yl)-N-ethyl-3-((3,3,3-trifluoropropyl)thio)propanamide (Compound 6.3):

To 3-neck round bottomed flask (50 mL) was added sodium hydride (60% in oil, 0.130 g, 3.28 mmol) and sulfolane (16 mL). The gray suspension was stirred for 5 minutes then N-(3-chloro-1-(pyridin-3-yl)-1H-pyrazol-4-yl)-3-((3,3,3-trifluoropropyl)thio)propanamide (1.20 g, 3.16 mmol) dissolved in sulfolane (25 mL) was slowly added dropwise over 5 minutes. The mixture became a light gray suspension after 3 minutes and was allowed to stir for 5 minutes after which time ethyl bromide (0.800 mL, 10.7 mmol) and potassium iodide (0.120 g, 0.720 mmol) were added sequentially. The cloudy suspension was then allowed to stir at room temperature. The reaction was quenched after 6 hours by being poured drop-wise into cooled ammonium formate/acetonitrile solution (30 mL). The resulting orange colored solution was stirred and tetrahydrofuran (40 mL) was added. The mixture was assayed, using octanophenone as a standard, and found to contain 1.09 g (85%) of the desired product with a selectivity versus the retry-Michael-like decomposition product of 97:3.

Example 7 N-(3-chloro-1-(pyridin-3-yl)-1H-pyrazol-4-yl)-N-ethyl-3-((3,3,3-trifluoropropyl)sulfoxo)propanamide (Compound 7.3)

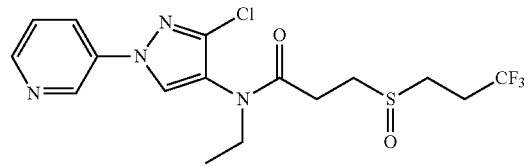 [SMILES: CCN(C(=O)CCS(=O)CCC(F)(F)F)c1cn(-c2cccnc2)nc1Cl]

N-(3-chloro-1-(pyridin-3-yl)-1H-pyrazol-4-yl)-N-ethyl-3-(3,3,3-trifluoropropypthio) propanamide (57.4 g, 141 mmol) was stirred in methanol (180 mL). To the resulting solution was added hydrogen peroxide (43.2 mL, 423 mmol) dropwise using a syringe. The solution was stirred at room temperature for 6 hours, at which point LCMS analysis indicated that the starting material was consumed. The mixture was poured into dichloromethane (360 mL) and washed with aqueous sodium carbonate. The organic layer was dried over sodium sulfate and concentrated to provide a thick yellow oil. The crude product was purified by flash column chromatography using 0-10% methanol/ethyl acetate as eluent and the pure fractions were combined and concentrated to afford the desired product as an oil (42.6 g, 68%): $^1$H NMR (400 MHz, DMSO-$d_6$) δ 9.09 (dd, J=2.8, 0.7 Hz, 1H), 8.98 (s, 1H), 8.60 (dd, J=4.7, 1.4 Hz, 1H), 8.24 (ddd, J=8.4, 2.7, 1.4 Hz, 1H), 7.60 (ddd, J=8.4, 4.7, 0.8 Hz, 1H), 3.61 (q, J=7.4, 7.0 Hz, 2H), 3.20-2.97 (m, 2H), 2.95-2.78 (m, 2H), 2.76-2.57 (m, 2H), 2.58-2.45 (m, 2H), 1.09 (t, J=7.1 Hz, 3H); ESIMS m/z 423 ([M+H]$^+$).

Example 8 3-((3,3,3-trifluoropropyl)thio)propanoyl chloride

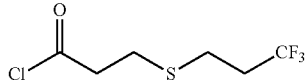 [SMILES: O=C(Cl)CCSCCC(F)(F)F]

A dry 5 L round bottom flask equipped with magnetic stirrer, nitrogen inlet, reflux condenser, and thermometer, was charged with 3-((3,3,3-trifluoropropyl)thio)propanoic acid (188 g, 883 mmol) in dichloromethane (3 L). Thionyl chloride (525 g, 321 mL, 4.42 mol) was then added dropwise over 50 minutes. The reaction mixture was heated to reflux (about 36° C.) for 2 hours, then cooled to room temperature. Concentration under vacuum on a rotary evaporator, followed by distillation (40 Torr, product collected from 123-127° C.) gave the title compound as a clear colorless liquid (177.3 g, 86%): $^1$H NMR (400 MHz, CDCl$_3$) δ 3.20 (t, J=7.1 Hz, 2H), 2.86 (t, J=7.1 Hz, 2H), 2.78-2.67 (m, 2H), 2.48-2.31 (m, 2H); $^{19}$F NMR (376 MHz, CDCl$_3$) δ −66.42, −66.43, −66.44, −66.44.

Example 9
3-(((2,2-difluorocyclopropyl)methyl)thio)propanoic acid

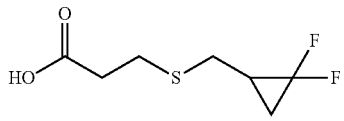 [SMILES: O=C(O)CCSCC1CC1(F)F]

Powdered potassium hydroxide (423 mg, 7.54 mmol) and 2-(bromomethyl)-1,1-difluorocyclopropane (657 mg, 3.84 mmol) were sequentially added to a stirred solution of 3-mercaptopropanoic acid (400 mg, 3.77 mmol) in methanol (2 mL) at room temperature. The resulting white suspension was stirred at 65° C. for 3 hours and quenched with 1 N aqueous hydrochloric acid and diluted with ethyl acetate. The organic phase was separated and the aqueous phase extracted with ethyl acetate (2×50 mL). The combined organic extracts were dried over magnesium sulfate, filtered and concentrated in vacuo to give the title molecule as a colorless oil (652 mg, 84%): IR (KBr thin film) 3025, 2927, 2665, 2569, 1696 cm$^{-1}$; $^1$H NMR (400 MHz, CDCl$_3$) δ 2.85 (t, J=7.0 Hz, 2H), 2.82-2.56 (m, 4H), 1.88-1.72 (m, 1H), 1.53 (dddd, J=12.3, 11.2, 7.8, 4.5 Hz, 1H), 1.09 (dtd, J=13.1, 7.6, 3.7 Hz, 1H); ESIMS in/z 195.1 ([M−H]$^-$).

Example 10
3-(((2,2-difluorocyclopropyl)methyl)thio)propanoyl chloride

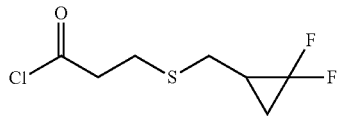 [SMILES: O=C(Cl)CCSCC1CC1(F)F]

In a 3 L 3-neck round bottomed-flask equipped with an overhead stirrer, a temperature probe, and addition funnel and an nitrogen inlet was charged with 3-(((2,2-difluorocyclopropyl)methyl)thio)propanoic acid (90.0 g, 459 mmol) that was immediately taken up in dichloromethane (140 mL) with stirring. At room temperature, thionyl chloride (170 mL, 2293 mmol) in dichloromethane (100 mL) was added drop-wise with stirring. The reaction mixture was heated to 40° C. and heated for 2 hours. The reaction was determined to be complete by $^1$H NMR (An aliquot of the reaction mixture was taken, and concentrated down via rotary evaporator). The reaction was allowed to cool to room temperature and the mixture was transferred to a dry 3 L round bottomed flask and concentrated via the rotary evaporator. This resulted in honey-colored oil (95 g). The contents were gravity filtered through paper and the paper rinsed with diethyl ether (10 mL). The rinse was added to the flask. This gave a clear yellow liquid. The liquid was placed on a rotary evaporator to remove the ether. This gave a yellow oil (92.4 g). The oil was Kugelrohr distilled (bp 100-110° C./0.8-0.9 mm Hg) to provide the title compound as a colorless oil (81.4 g, 81%): $^1$H NMR (400 MHz, CDCl$_3$) δ 3.27-3.12 (m, 2H), 2.89 (t, J=7.1 Hz, 2H), 2.67 (ddd, J=6.8, 2.6, 1.0 Hz, 2H), 1.78 (ddq, J=13.0, 11.3, 7.4 Hz, 1H), 1.64-1.46 (m, 1H), 1.09 (dtd, J=13.2, 7.7, 3.7 Hz, 1H).

BIOLOGICAL EXAMPLES

Example A Bioassays on Green Peach Aphid ("GPA") (*Myzus persicae*) (MYZUPE

GPA is the most significant aphid pest of peach trees, causing decreased growth, shriveling of leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, macadamia, papaya, peppers, sweet potatoes, tomatoes, watercress and zucchini among other plants. GPA also attacks many ornamental crops such as carnations, chrysanthemum, flowering white cabbage, poinsettia and roses. GPA has developed resistance to many pesticides.

Several molecules disclosed herein were tested against GPA using procedures described below.

Cabbage seedling grown in 3-in pots, with 2-3 small (3-5 cm) true leaves, were used as test substrate. The seedlings were infested with 20-5-GPA (wingless adult and nymph stages) one day prior to chemical application. Four pots with individual seedlings were used for each treatment. Test compounds (2 mg) were dissolved in 2 mL of acetone/MeOH (1:1) solvent, forming stock solutions of 1000 ppm test compound. The stock solutions were diluted 5× with 0.025% Tween 20 in water to obtain the solution at 200 ppm test compound. A hand-held aspirator-type sprayer was used for spraying a solution to both sides of the cabbage leaves until runoff. Reference plants (solvent check) were sprayed with the diluent only containing 20% by volume acetone/MeOH (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol 18 (1925), pp. 265-267) as follows.

Corrected % Control=100*(X−Y)/X where

X=No. of live aphids on solvent check plants and
Y=No. of live aphids on treated plants The results are indicated in the table entitled "Table 1: GPA (MYZUPE) and sweetpotato whitefly-crawler (BEMITA) Rating Table".

Example B Bioassays on Sweetpotato Whitefly Crawler (*Bernisia tabaci*) (BEMITA.)

The sweetpotato whitefly, *Bernisia tabaci* (Gennadius), has been recorded in the United States since the late 1800s. In 1986 in Florida, *Bernisia tabaci* became an extreme economic pest. Whiteflies usually feed on the lower surface of their host plant leaves. From the egg hatches a minute crawler stage that moves about the leaf until it inserts its microscopic, threadlike mouthparts to feed by sucking sap from the phloem. Adults and nymphs excrete honeydew (largely plant sugars from feeding on phloem), a sticky, viscous liquid in which dark sooty molds grow. Heavy infestations of adults and their progeny can cause seedling death, or reduction in vigor and yield of older plants, due simply to sap removal. The honeydew can stick cotton lint together, making it more difficult to gin and therefore reducing its value. Sooty mold grows on honeydew-covered substrates, obscuring the leaf and reducing photosynthesis, and reducing fruit quality grade. It transmitted plant-pathogenic viruses that had never affected cultivated crops and induced plant physiological disorders, such as tomato irregular ripening and squash silverleaf disorder. Whiteflies are resistant to many formerly effective insecticides.

Cotton plants grown in 3-inch pots, with 1 small (3-5 cm) true leaf, were used at test substrate. The plants were placed in a room with whitely adults. Adults were allowed to deposit eggs for 2-3 days. After a 2-3 day egg-laying period, plants were taken from the adult whitefly room. Adults were blown off leaves using a hand-held Devilbliss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in water to obtain a test solution at 200 ppm. A hand-held Devilbliss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Insecticidal activity was measured by using Abbott's correction formula (see above) and presented in Table 1.

TABLE 1

| GPA (MYZUPE) and sweetpotato whitefly-crawler (BEMITA) Rating Table | | |
|---|---|---|
| Example Compound | BEMITA | MYZUPE |
| 1a | B | B |
| Compound 2.3 | B | B |
| Compound 5.3 | B | A |
| Compound 6.3 | A | A |
| Compound 7.3 | A | A |

| % Control of Mortality | Rating |
|---|---|
| 80-100 | A |
| More than 0 - Less than 80 | B |
| Not Tested | C |
| No activity noticed in this bioassay | D |

COMPARATIVE EXAMPLES

Example CE-1
N-(1-Acetyl-1H-pyrazol-4-yl)acetamide

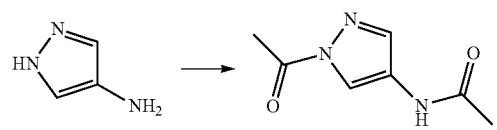

A 250-mL 3-neck flask was charged with 1H-pyrazol-4-amine (5 g, 60.2 mmol) and dichloromethane (50 mL). The resulting suspension was cooled to 5° C. and triethylamine (9.13 g, 90.0 mmol) was added, followed by acetic anhydride (7.37 g, 72.2 mmol) at <20° C. The reaction was stirred at room temperature for 18 hours, at which point thin layer chromatography (Eluent: ethyl acetate) analysis indicated that the reaction was incomplete. Additional triethylamine (4.57 g, 45.0 mmol) and acetic anhydride (3.70 g, 36.0 mmol) were added and the reaction was heated at 30° C. for an additional 3 hours to give a dark solution, at which point thin layer chromatography analysis indicated that only a trace of starting material remained. The reaction mixture was purified by flash column chromatography using ethyl acetate as eluent. The fractions containing pure product were combined and concentrated to dryness to afford an off-white solid. The solid was dried under vacuum at room temperature for 18 hours (5.55 g, 55%): $^1$H NMR (400 MHz, DMSO-$d_6$) δ 10.30 (s, 1H), 8.39 (d, J=0.7 Hz, 1H), 7.83 (d, J=0.7 Hz, 1H), 2.60 (s, 3H), 2.03 (s, 3H); EIMS m/z 167 ([M]$^+$).

Example CE-2
N-(3-Bromo-1H-pyrazol-4-yl)acetamide

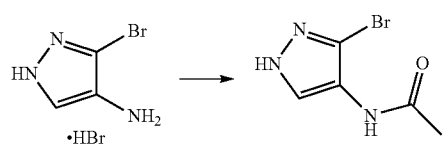

A 250 mL 3-neck round bottom flask was charged with 1H-pyrazol-4-amine-hydrobromide (4.00 g, 24.7 mmol) and water (23 mL). To the mixture, sodium bicarbonate (8.30 g, 99.0 mmol) was added slowly over 10 minutes, followed by tetrahydrofuran (23 mL). The mixture was cooled to 5° C. and acetic anhydride (2.60 g, 25.4 mmol) was added over 30 minutes while maintaining the internal temperature at <10° C. The reaction mixture was stirred at ~5° C. for 20 minutes, at which point $^1$HNMR and UPLC analyses indicated that the starting material was consumed and the desired product as well as bis-acetylated byproduct were formed. The reaction was extracted with ethyl acetate and the organic layers were dried over magnesium sulfate and concentrated. The crude mixture was triturated with methyl tert-butylether to remove the bisacetylated product to afford ~1.24 g of a white solid. $^1$H NMR analysis showed it was 1:1.1 desired to undesired bisacetylated product. The solid was purified by flash column chromatography using 50-100% ethyl acetate/hexanes as eluent to afford the desired product as a white solid (380 mg, 7.5%) and the bisacetylated product as a white solid (~800 mg): $^1$H NMR (400 MHz, DMSO-d$_6$) δ 13.01 (s, 1H), 9.36 (s, 1H), 7.92 (s, 1H), 2.03 (s, 3H); $^{13}$C NMR (101 MHz, DMSO) δ 167.94, 123.93, 119.19, 119.11, 22.63; ESIMS m/z 204 ([M+H]$^+$).

Example CE-3 Alkylation Versus
Retry-Michael-Like Decomposition

A suspension of sodium hydride (60% in oil, 1.03 eq) and solvent (1 vol) was stirred for 5 minutes N-(3-Chloro-1-(pyridin-3-yl)-1H-pyrazol-4-yl)-3-(3,3,3-trifluoropropyl)thio)-propanamide (1 eq) dissolved in solvent (2 vol) was slowly added dropwise over 5 minutes. Ethyl bromide (3.3 eq) and additive (0.22 eq) were added sequentially. The suspension was then allowed to stir at room temperature until consumption of starting material was observed. The selectivity of Compound 6.3 over the decomposition product was determined by HPLC (See Table 2).

TABLE 2

| Entry | Additive | Solvent | Time (hours) | Compound 6.3: Decomposition Product |
|---|---|---|---|---|
| 1 | tetrabutyl-ammonium iodide | N,N-dimethylformamide | 24 | 81:19 |
| 2 | potassium iodide | N,N-dimethylformamide | 72 | 94:6 |
| 3 | potassium iodide | N-methylpyrolidinone | 20 | 92:8 |

It should be understood that while this invention has been described herein in terms of specific embodiments set forth in detail, such embodiments are presented by way of illustration of the general principles of the invention, and the invention is not necessarily limited thereto.

Certain modifications and variations in any given material, process step or chemical formula will be readily apparent to those skilled in the art without departing from the true spirit and scope of the present invention, and all such modifications and variations should be considered within the scope of the claims that follow.

What is claimed is:
1. A compound N-(3-chloro-1H-pyrazol-4-yl)-3-((3,3,3,trifluoropropyl)thio)propanamide (Compound 2.3)

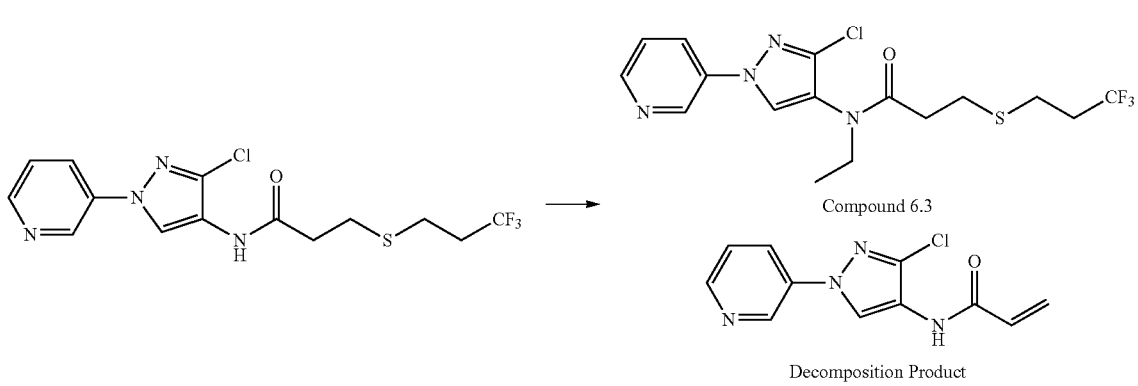 [SMILES: O=C(CCSCCC(F)(F)F)Nc1cn(-c2cccnc2)nc1Cl ; CCN(C(=O)CCSCCC(F)(F)F)c1cn(-c2cccnc2)nc1Cl ; C=CC(=O)Nc1cn(-c2cccnc2)nc1Cl]

Compound 6.3

Decomposition Product

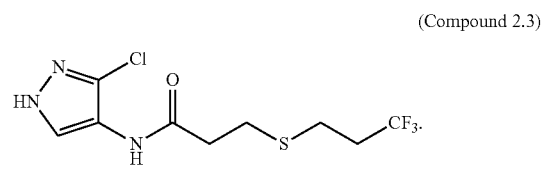 [SMILES: O=C(CCSCCC(F)(F)F)Nc1c[nH]nc1Cl]

(Compound 2.3)

* * * * *